United States Patent [19]

Wolf et al.

[11] Patent Number: 4,744,953
[45] Date of Patent: May 17, 1988

[54] BREATH FLOW INDICATOR

[75] Inventors: Karl P. Wolf, Webster Groves; Macquorn R. Forrester, St. Louis, both of Mo.

[73] Assignee: Intoximeters, Inc., St. Louis, Mo.

[21] Appl. No.: 7,508

[22] Filed: Jan. 28, 1987

[51] Int. Cl.[4] ............................................. G01N 1/22
[52] U.S. Cl. ............................. 422/84; 116/137 R; 436/132
[58] Field of Search .............. 73/27 R, 23; 116/137 R; 422/84, 85; 436/132, 900; 446/204–207, 213–216

[56] References Cited

U.S. PATENT DOCUMENTS 735,628  8/1903  Waxel ..................... 116/137 R X
3,877,291  4/1975  Hoppesch et al. ............. 340/634 X Primary Examiner—Barry S. Richman
Assistant Examiner—Michael S. Gzybowski
Attorney, Agent, or Firm—Polster, Polster and Lucchesi

[57] ABSTRACT

In a portable breath alcohol detector using a standard tubular mouthpiece, a breath direction and continuity sensor takes the form of a whistle mounted at a predetermined distance from the discharge end of the mouthpiece to leave a gap, open to the ambient atmosphere, between the discharge end and the whistle, the whistle being of sufficient sensitivity to be activated by a breath blown toward the whistle across the gap and the gap being of a size not appreciably to restrict the flow of breath, and permit air being inhaled to pass freely, whereby if the subject stops breathing, or inhales, the whistle stops sounding, and whereby residual alcohol in the whistle will not be drawn back into the mouthpiece when the subject inhales.

4 Claims, 1 Drawing Sheet

BREATH FLOW INDICATOR

BACKGROUND OF THE INVENTION

This invention relates to portable breath alcohol detectors of the type sold under the trademark ALCO-SENSOR by Intoximeters, Inc., of St. Louis, Mo., which use a standard tubular mouthpiece of a type described generally in Jones et al. U.S. Pat. No. 3,940,251, a straight cylinder with a small hole mid-way of its length, thru which projects a stub tube mounted on an upper wall of the housing of the detector. Heretofore, a subject whose breath is to be tested blows through the tube, and either after a predetermined period or when the operator thinks that the subject is exhaling deep lung breath, the operator causes a sample to be taken of the passing breath, the sample being sucked through the stub tube, in a metered amount, into a fuel cell that may be of the type described in Wolf U.S. Pat. No. 4,487,055.

If the sampling time is determined by the Police Officer, it is often under somewhat difficult circumstances. It may be dark, and the subject is likely to be uncooperative. Accordingly, the Officer is not able easily to tell if the subject has stopped blowing momentarily or has inhaled, either of which will jeopardize the proper results of the test.

Audible signals in connection with breath testing equipment have been described heretofore. However, those devices had a disadvantage of being liable to sound when the subject inhales, and of trapping breath alcohol which is brought back into the system when the subject inhales.

One of the objects of this invention is to provide an audible signal indicating that the subject is blowing into the mouthpiece, that stops sounding when the subject either stops blowing or inhales, and at the same time does not permit residual alcohol from a previous test to be introduced to the mouthpiece upon inhalation by the subject.

Another object is to provide such a device that creates no substantial impediment to the flow of breath nor introduces ambient air into the breath stream.

Yet another object is to provide such a device that is simple and that automatically assures the proper orientation of the mouthpiece.

Other objects will become apparent to those skilled in the art in the light of the following description and accompanying drawing.

SUMMARY OF THE INVENTION

In accordance with this invention, generally stated, a breath direction and continuity sensor is provided for a portable breath alcohol detector wherein a tubular mouthpiece is mounted on one end of a housing of the detector, the mouthpiece having a breath inlet and a breath outlet end when mounted on the housing. The sensor comprises a whistle mounted on the housing at a predetermined distance from the discharge end of the mouthpiece to leave a gap open to the ambient atmosphere between the discharge end and the whistle. The gap is of a size and the whistle is of a sufficient sensitivity so that the whistle is activated by breath blown toward the whistle across the gap but does not restrict the flow of breath appreciably. The gap is sufficiently wide to permit air being inhaled to pass freely, whereby residual alcohol in the whistle will not be drawn back into the mouthpiece when a subject inhales. The whistle will stop sounding when the subject being tested either stops blowing or inhales. In the preferred embodiment described, the whistle is held in a whistle mount which comprises a trough portion to receive the discharge end of the mouthpiece and align it with the whistle, and a whistle-holding portion in which the whistle is held in spaced relation to the discharge end of the mouthpiece when the mouthpiece is seated in the trough portion.

DESCRIPTION OF THE PREFERRED EMBODIMENT

Figure 1:
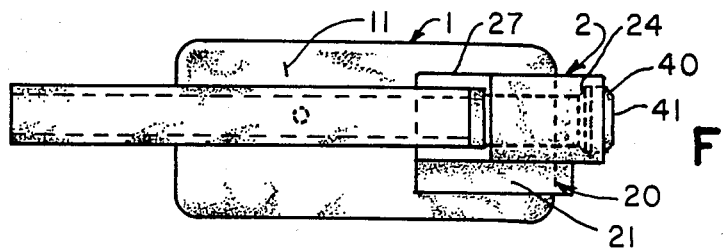
FIG. 1 is a top plan view of a breath alcohol detector on which a sensor of one illustrative embodiment of this invention is mounted.
Figure 2:
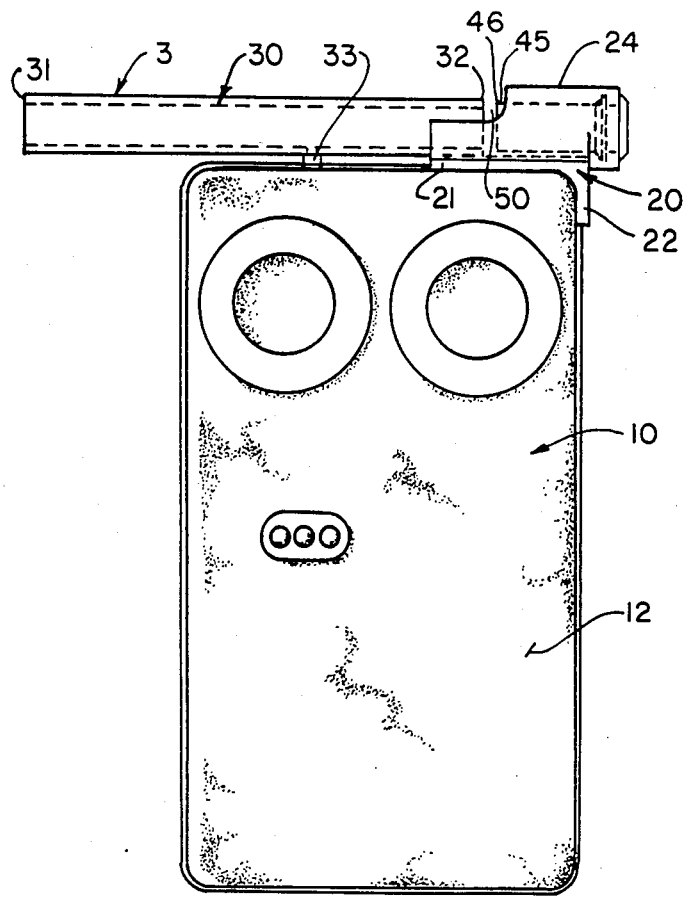
FIG. 2 is a view in side elevation.
Figure 3:
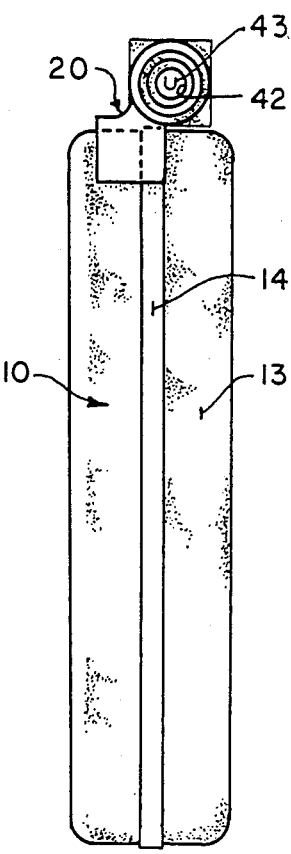
FIG. 3 is a view in end elevation.
Figures 4, 5, 6:
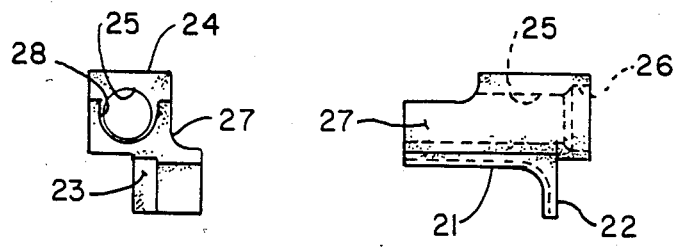
FIG. 4 is a view in end elevation viewed from left to right in the orientation shown in FIG. 1, of a whistle mount unattached to the housing.
FIG. 5 is a view in side elevation of the mount shown in FIG. 4.
FIG. 6 is a view in end elevation as viewed from right to left in FIGS. 1 and 2 of the mount shown in FIG. 4.

Referring now to the drawings for one illustrative embodiment of this invention, reference numeral 1 indicates a portable breath alcohol detector of the type sold under the trademark ALCO-SENSOR by Intoximeters, Inc., on which a breath sensor 2 is mounted. A standard mouthpiece 3 of the type described generally in Jones, et al. U.S. Pat. No. 3,940,251, is also mounted on the detector 1.

The detector itself includes a housing 10 with a top surface 11, a bottom surface, not shown, a front surface 12, a substantially planer rear surface, not shown, edge surfaces 13, and a rib 14 extending around the housing to define a frame within which the open edge of half of the housing is received. A mounting tube 33, community at an inner end with a fuel cell, projects upwardly from and through the top surface 11.

In this embodiment, the breath sensor 2 includes a base 20 with a top engaging part 21 and a depending leg 22. A channel 23 in the underside of the top engaging part and the leg accommodates the rib 14, and serves, with the rib, as a locating means transversely of the width of the top surface 11. A whistle holder portion 24 is carried by the top engaging part 21, offset laterally from the center line of the top engaging part and leg, but parallel to the front and rear surfaces of the housing. A cylindrical passage 25 extends through the portion 24, and has at its end adjacent leg 22 a counterbore 26. A trough portion 27 extends inboardly from the whistle holder portion. The trough portion 27 defines a trough 28, semi-circular in elevation, co-axial with the cylindrical passage 25 but of a slightly larger radius, complementary to the radius of the outside surface of a discharge end 32 of a tube 30 comprising the mouthpiece 3. The tube 30 is a straight cylinder, with an inlet end 31 opposite the discharge end 32, and a radial passage for the stub tube 33 communicating with the interior of the tube 30 and, by way of the tube 33, with the fuel cell within the housing 10.

A whistle 40 is mounted in the whistle holder portion 24. In this embodiment, the whistle includes a barrel 45, at one end of which is a circular frame 41, framing a diaphragm or web 42, from which a reed 43 is lanced. The circular frame 41 is of larger diameter than the barrel 45. The barrel fits snugly within the passage 25, and the circular frame within the counterbore 26. An inner end 46 of the barrel 45 projects slightly into the trough 28, and is spaced from the discharge end 32 of the mouthpiece to define a gap 50 between them. The width of the gap 50 can be determined accurately by the length of the barrel 45, the frame 41, seating in the counterbore 26, locating the end 46 of the barrel 45.

In this embodiment, all of the elements 20–28 are molded in one piece, of a suitable dimensionally stable plastic. In this embodiment, the resultant assembly is secured to the housing by means of a suitable adhesive, but it could be made integral with one half of the housing itself.

In operation, the conventional mouthpiece is mounted on the stub tube 33 on the housing, with its discharge end seated in the trough 28. When a subject blows through the tube, the reed 43 vibrates to produce an audible signal indicating that the subject is blowing with sufficient force to make the sound. If the sound stops, the subject has either stopped blowing, or has inhaled. In either event, the operator knows that the subject will have to be required to start over again. When a continuous signal has been heard for the required length of time, and while the blowing continues as indicated by the audible signal, the sampling system is actuated. There is, of course, a slight back pressure required to actuate the reed, but that can be negligible. On the other hand, when the subject inhales, even the slight resistance of the reed is sufficient to insure that the inhaled ambient air is drawn through the gap 50, and not through the whistle barrel 45.

Numerous variations in the construction of the device of this invention, within the scope of the appended claims, will occur to those skilled in the art in the light of the foregoing disclosure. Merely by way of illustration, the shape and size of the breath sensor can be modified, and the type of whistle varied. These are merely illustrative.

Having thus described the invention, what is claimed and desired to be secured by Letters Patent is:

1. In a portable breath alcohol detector wherein a tubular mouthpiece is mounted on one end of a housing, said mouthpiece having a breath inlet and a breath discharge end when mounted on said housing, the improvement comprising a breath direction and continuity sensor comprising a whistle mounted on said housing at a predetermined distance from said discharge end of said mouthpiece to leave a gap opened to the ambient atmosphere between said discharge end and said whistle, said gap being of a size and said whistle being sufficiently sensitive to be activated by breath blown toward said whistle across said gap with a force sufficient to provide an adequate breath sample when maintained for a predetermined period but not appreciably to restrict the flow of breath and said gap being sufficiently wide to permit air being inhaled to pass freely through it and into the said mouthpiece, whereby residual alcohol in said whistle will not be drawn back into said mouthpiece when a subject inhales.

2. The sensor of claim 1 wherein the whistle is a reed type whistle and serves as a check valve upon inhalation by the subject.

3. The sensor of claim 1 including a whistle mount comprising a trough portion to receive the discharge end of the mouthpiece and align it with the whistle, and a whistle-holding portion in which the whistle is held in spaced relation to the discharge end of the mouthpiece when it is seated in said trough portion.

4. The sensor of claim 3 wherein the said detector housing is generally rectangular with a relatively short top and bottom wall and long side walls, at least one of said side walls and top wall having a rib extending along them along which said housing opens, and an opening in said top wall from which a stub tube extends radially into said mouthpiece, said whistle mount having a base with a top engaging portion and a depending leg portion, said base being offset from a longitudinal center line of said trough, said base having a channel to accommodate said rib and locate said trough parallel with the center line of said top.

* * * * *